(12) United States Patent
Bucki et al.

(10) Patent No.: US 9,008,381 B2
(45) Date of Patent: Apr. 14, 2015

(54) IMAGE PROCESSING METHOD FOR ESTIMATING A BRAIN SHIFT

(75) Inventors: Marek Bucki, La Tronche (FR); Yohan Payan, Allevard (FR)

(73) Assignees: Universite Joseph Fourier—Grenoble 1, St. Martin d'Héres (FR); Centre National de la Recherche Scientifique (CNRS), Paris (FR)

( * ) Notice: Subject to any disclaimer, the term of this patent is extended or adjusted under 35 U.S.C. 154(b) by 121 days.

(21) Appl. No.: 13/122,092

(22) PCT Filed: Oct. 2, 2009

(86) PCT No.: PCT/EP2009/062826
§ 371 (c)(1),
(2), (4) Date: Jun. 15, 2011

(87) PCT Pub. No.: WO2010/037850
PCT Pub. Date: Apr. 8, 2010

(65) Prior Publication Data
US 2011/0257514 A1 Oct. 20, 2011

(30) Foreign Application Priority Data
Oct. 3, 2008 (FR) ..................................... 08 56712

(51) Int. Cl.
*G06K 9/00* (2006.01)
*G06T 7/00* (2006.01)
*A61B 8/08* (2006.01)

(52) U.S. Cl.
CPC ..... *G06T 7/0038* (2013.01); *G06T 2207/10072* (2013.01); *G06T 2207/30016* (2013.01); *A61B 8/0808* (2013.01)

(58) Field of Classification Search
None
See application file for complete search history.

(56) References Cited

U.S. PATENT DOCUMENTS

| | | |
|---|---|---|
| 7,072,705 B2 | 7/2006 | Miga et al. |
| 7,103,399 B2 | 9/2006 | Miga et al. |

(Continued)

FOREIGN PATENT DOCUMENTS

WO   WO 2005/025404   3/2005

OTHER PUBLICATIONS

Miga, M.I., Roberts, D.W., Kennedy, F.E., Platenik, L.A., Hartov, A., Lunn, K.E., and Paulsen, K.D., Modeling of Retraction and Resection for Intraoperative Updating of Images, 2001, Neurosurgery, vol. 49, No. 1, pp. 75-85.*

(Continued)

*Primary Examiner* — Stephen R Koziol
*Assistant Examiner* — Jonathan S Lee
(74) *Attorney, Agent, or Firm* — Harness, Dickey & Pierce, P.L.C.

(57) ABSTRACT

The disclosure relates to an image processing method for estimating a brain shift in a patient, the method involving: the processing of a three-dimensional image of the brain of a patient, acquired before a surgical operation, in order to obtain a reference cerebral arterial tree structure of the patient; the processing of three-dimensional images of the brain of the patient, acquired during the operation, in order to at least partially reconstitute a current cerebral arterial tree structure of the patient; the determination from the combination of the reference and current cerebral arterial tree structures, of a field of shift of the vascular tree representing the shift of the current vascular tree in relation to the reference vascular tree; the application of the determined field of shift of the vascular tree to a biomechanical model of the brain of the patient in order to estimate the brain shift of the patient; and the generation, from the estimated brain shift, of at least one image of the brain of the patient, in which the brain shift is compensated.

20 Claims, 5 Drawing Sheets

(56) References Cited

U.S. PATENT DOCUMENTS

| | | | |
|---|---|---|---|
| 7,647,087 B2 | | 1/2010 | Miga et al. |
| 8,233,681 B2 * | | 7/2012 | Aylward et al. ............... 382/128 |
| 8,388,539 B2 * | | 3/2013 | Yamamoto et al. ........... 600/443 |
| 2005/0101855 A1 * | | 5/2005 | Miga et al. .................... 600/407 |
| 2005/0148859 A1 * | | 7/2005 | Miga et al. .................... 600/410 |
| 2005/0245810 A1 * | | 11/2005 | Khamene et al. ............. 600/410 |
| 2005/0272991 A1 * | | 12/2005 | Xu et al. ........................ 600/407 |
| 2006/0036167 A1 | | 2/2006 | Shina |
| 2007/0021669 A1 | | 1/2007 | Miga et al. |
| 2007/0083117 A1 * | | 4/2007 | Sakas et al. ................... 600/437 |
| 2007/0238952 A1 * | | 10/2007 | Boese et al. ................... 600/407 |
| 2008/0247622 A1 * | | 10/2008 | Aylward et al. ............... 382/131 |

OTHER PUBLICATIONS

Ji, S., Hartov, A., Roberts, D., and Paulsen, K., Mutual-Information-Corrected Tumor Displacement using Intraoperative Ultrasound for Brain Shift Compensation in Image-Guided Neurosurgery, 2008, Medical Imaging 2008: Visualization, Image-guided Procedures, and Modeling, vol. 6918, pp. 1-12.*

Comeau, R.M., Sadikot, A.F., Fenster, A., and Peters, T.M., Intraoperative ultrasound for guidance and tissue shift correction in image-guided neurosurgery, 2000, Am. Assoc. Phys. Med., vol. 24, No. 4, pp. 787-800.*

Clatz, O., Delingette, H., Talos, I.F., Golby, A.J., Kikinis, R., Jolesz, F.A., Ayache, N., and Warfield, S.K., Robust Nonrigid Registration to Capture Brain Shift from Intraoperative MRI, 2005, IEEE Transactions on Medical Imaging, vol. 24, No. 11, pp. 1417-1427.*

Iseki, H., Muragaki, Y., Nakamura, R., Hori, T., and Takahura, K., Computer Assisted Neurosurgery, 2006, Int J CARS, vol. 1, pp. 293-310.*

Jordan, P., Image-Based Mechanical Characterization of Soft Tissue using Three Dimensional Ultrasound, 2008, Undergraduate Thesis, Harvard University.*

Ho, J. and Kleiven, S., Dynamic response of the brain with vasculature: A three-dimensional computational study, 2007, Journal of Biomechanics, p. 3006-3012.*

Fang, B. and Tang, Y.Y., Elastic Registration for Retinal Images Based on Reconstructed Vascular Trees, Jun. 6 2006, IEEE Transactions on Biomedical Engineering, vol. 53, No. 6, pp. 1183-1187.*

Comeau, R.M., Sadikot, A.F., Fenster, A., and Peters, T.M., Intraoperative ultrasound for guidance and tissue shift correction in image-guided neurosurgery, 2000, Medical Physics, vol. 27, pp. 787-800.*

Bucki, M. et al,"Framework and Bio-Mechanical Model for a Per-Operative Image-Guided Neuronavigation Including 'Brain-Shift' Compensation;" http://hal.archives-ouvertes.fr/docs/00/10/85/09/PDF/Brainshift_Santiago.pdf; Oct. 23, 2006.

Bucki, M. et al, "Framework for a Low-Cost Intra-Operative Image-Guided Neuronavigator Including Brain Shift Compensation;" Engineering in Medicine and Biology Society, 2007; Aug. 22, 2007, pp. 872-875.

Armspach, J. et al, "3-D Deformable Image Registration: A Topology Preservation Scheme Based on Hierarchical Deformation Models and Interval Analysis Optimization;" IEEE Transactions in Image Processing, vol. 14, No. 5, May 1, 2005; pp. 553-566.

Noblet, V. et al, "Retrospective Evaluation of a Topology Preserving Non-Rigid Registration Method," Medical Image Analysis, Oxford University Press, vol. 10, No. 3, Jun. 1, 2006, pp. 366-384.

Miller, M. et al, "Group Actions, Homeomorphisms, and Matching: A General Framework," International Journal of Computer Vision, vol. 41, No. 1-2; Feb. 2001; pp. 61-84.

* cited by examiner

FIG. 3
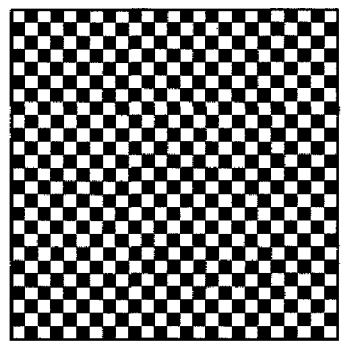
(a)
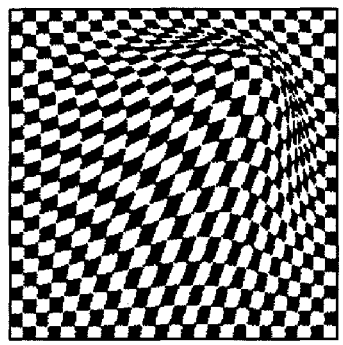
(b)
FIG. 4
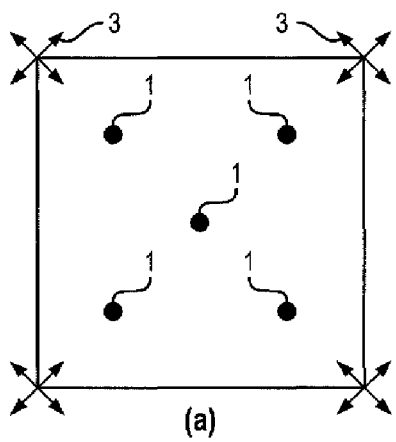
(a)
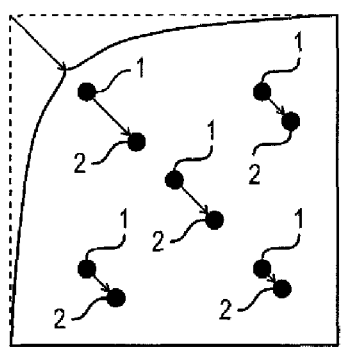
(b)
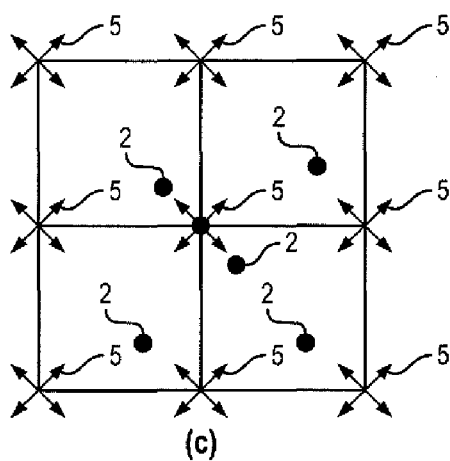
(c)
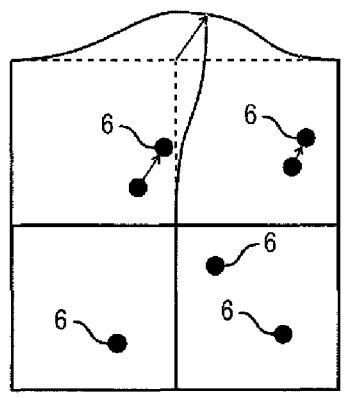
(d)

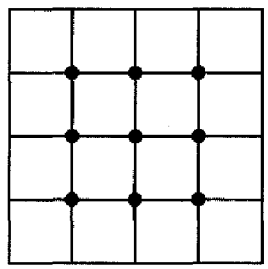
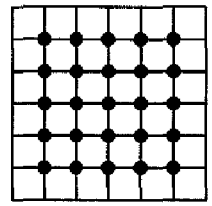
(a)           FIG. 5           (b)
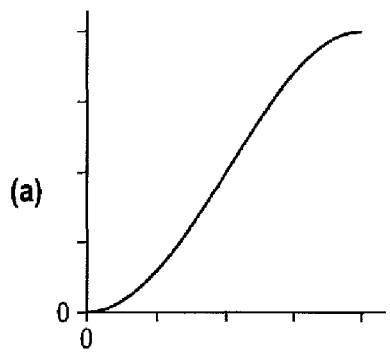
(a)
FIG. 6
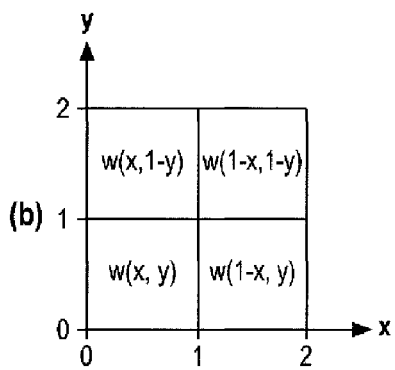
(b)
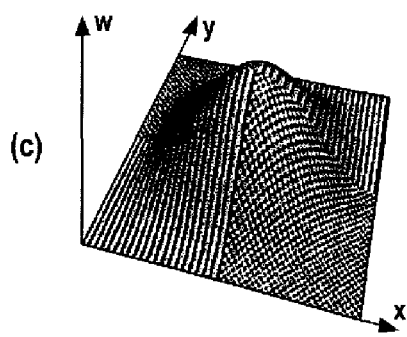
(c)

IMAGE PROCESSING METHOD FOR ESTIMATING A BRAIN SHIFT

CROSS-REFERENCE TO RELATED APPLICATIONS

This application is a National Phase Entry of International Application No. PCT/EP2009/062826, filed on Oct. 2, 2009, which claims priority to French Patent Application Serial No. 0856712, filed on Oct. 3, 2008, both of which are incorporated by reference herein.

FIELD OF THE INVENTION

The present invention relates to the field of computer-assisted neurosurgery, and more particularly a system and method for precise location of a target.

BACKGROUND

Precise location of a target is essential for reducing the morbidity rate during a surgical operation involving cerebral tumour ablation. During a surgical operation on the brain, a shift in cerebral tissues (or "brain shift" according to English terminology) can occur after an opening has been made in the cranium of the patient. This shift can be associated with physical phenomena (gravity, loss of cephalorachidian liquid, action by the neurosurgeon, etc.) or with physiological phenomena (tumefaction due to osmotic, anaesthetic drugs, etc.), some of which are still unknown.

Neuro-navigation systems have been developed to compensate for this brain shift of the patient and discover the preoperative data of the patient during the surgical procedure. These neuro-navigation systems display the position of surgical objects relative to the position of the anatomical cerebral characteristics of the patient for the surgeon. In this type of system the compensation of the brain shift of the patient is generally made on the following principle.

A first image of the cortical surface of the patient is acquired prior to the surgical operation. During the surgical operation, a second image of the cortical surface of the patient is acquired. Processing means of the system compare these two images and estimate a shift volume field which enables the points in the two images to be aligned to compensate for the brain shift of the patient. Such systems are especially described in documents U.S. Pat. No. 7,072,705 and U.S. Patent Publication No. 2007/0021669.

Yet, a disadvantage of this compensation technique of the brain shift of the patient from points of the cortical surface is that it leaves out a significant zone of the brain (under the cortical surface) in which the real brain shift is unknown. An aim of the present invention is to propose a system and a compensation process of the brain shift of the patient for rectifying at least one of the above disadvantages.

SUMMARY

For this purpose, the invention provides a passive navigation process for estimating a brain shift of a patient, the process comprising:
  processing of a three-dimensional image of the brain of the patient, acquired prior to a surgical operation, to obtain a reference cerebral arterial tree structure of the patient,
  processing of bidimensional images of the brain of the patient, acquired during the operation, to reconstitute at least partially a current cerebral arterial tree structure of the patient,
  determination, from the mapping of the reference and current cerebral arterial tree structures of a shift field of the vascular tree representing the shift of the current vascular tree relative to the reference vascular tree,
  application of the determined shift field of the vascular tree to a biomechanical model of the brain of the patient for estimating the brain shift of the patient.
  generation, from the estimated brain shift of at least one image of the brain of the patient in which the brain shift is compensated. The initial vascular tree is recalibrated elastically to its deformed configuration, segmented into the focussed US Doppler images, and the resulting shift field is then extended to the entire volume of the organ by means of a biomechanical model specific to the patient.

The overall shift calculated in this way reveals the preoperative data and rectifies the initial surgical planning. The invention provides the surgeon with a rapid, robust and precise response and gives him the possibility of validating the pertinence of the calculated shift prior to any planning modification.

Preferred though non-limiting aspects of the present invention are the following:
  the process can also comprise calculating disparities between points of the generated image of the brain and one or more bidimensional control images acquired during the operation;
  the three-dimensional image acquired prior to the operation can be a magnetic resonance angiography, the bidimensional images acquired during the operation can be ultrasound images in Doppler mode,
  the processing of the three-dimensional image to obtain the reference cerebral arterial tree structure comprises an orientation step of the three-dimensional image relative to the head of the patient after the installation of the latter on an operating table,
  the orientation step of the three-dimensional image comprises:
    locating a set of calibration points on the head of the patient after installation of the latter on the operating table,
    detecting their radiometric isologues in the three-dimensional image, and
    determine rigid transformations for moving positions of the points of the set of calibration points to the positions of their isologues in the three-dimensional image,
  the calibration points can comprise points of the surface of the head of the patient after the installation of the latter on the operating table,
  the processing of bidimensional images to reconstitute at least partially a current cerebral arterial tree structure of the patient comprises the segmentation of bidimensional images to obtain the median position of vessels and/or arteries of the brain so as to a reconstitute at least partially the current cerebral arterial tree structure of the patient, the step of determining a shift field comprises determination of non-linear transformations, called elastic transformations, for moving the positions of the points of the reference cerebral arterial tree structure to the positions of the points mapping of the current arterial tree structure.

The invention also relates to a system for determining a brain shift on a patient, the system comprising means for executing the process described hereinabove.

BRIEF DESCRIPTION OF THE FIGURES

Other advantages and characteristics will emerge more clearly from the following description of several variant embodiments given by way of non-limiting examples from the attached figures, in which:

FIG. 3 illustrates a shift of a unit square with folding of space;

FIG. 4 illustrates in two dimensions an iterative multi-scale approach described in relation to the step recalibration of organic tissue;

FIG. 5 illustrates cells inserted at the margin of digitalising for two successive levels of refinement;

FIG. 6 illustrates a function of form w;

DETAILED DESCRIPTION OF THE INVENTION

An embodiment of the process according to the invention will now be described in greater detail.

General Principle of the Invention

As explained previously, precise location of the surgical target is essential for reducing the morbidity during surgical exercises of a cerebral tumour. When the dimensions of the craniotomy are substantial a shift in the soft tissue of the brain can occur during the intervention. Due to this brain shift, the preoperative data no longer correspond to reality, and neuronavigation is considerably compromised as a result. The present invention takes this shift into consideration and calculates a rectified position of the anatomical structures of the brain to locate the auxiliaries.

Prior to a surgical operation on the brain of a patient, a magnetic resonance angiography (MRA) of the brain of the patient can be acquired. During the intervention, as a result of a significant brain shift the surgeon carries out echographic Doppler scanning of the region of interest.

The invention proposes a technique for updating preoperative data as a function of the brain shift during the intervention. For this to happen, the invention proposes following the shift in the particular anatomical structure which is the cerebral vascular tree during the intervention. Due to its distribution in the volume of the parenchyma, the shifts of the vascular tree are representative of overall shifts in tissue. In fact, the arteries and arterioles irrigating the nerve tissues are present at the same time in the deep parts of the encephalon, but also at the surface, and more particularly near the tumour the development of which passes via angiogenesis and therefore the formation of new vessels.

It is possible to deduce the shifts of its vessels, caused by the brain shift, from location of the vascular tree relative to its initial position at the start of intervention. This information, far from being dense in overall volume, remains localised to some regions. The invention proposes using biomechanical modelling of the brain of the patient to extrapolate a global shift from the shift of the cerebral vascular tree. The resulting field of global shifts is then transferred to all the preoperative data for updating.

Description of an Embodiment of the Process According to the Invention

Figure 1:
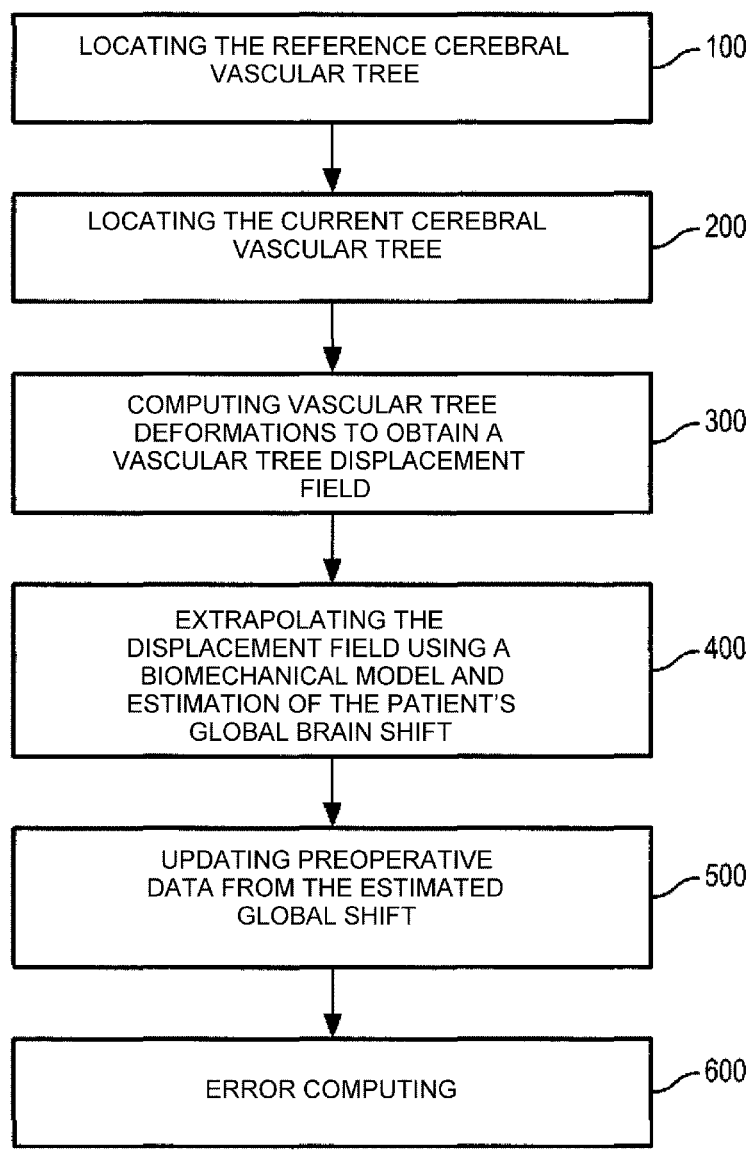
FIG. 1 illustrates an embodiment of the process according to the invention.

In reference to FIG. 1, this illustrates different steps of the process according to the invention. The image-treatment process for estimating a brain shift of a patient comprises the following steps:

processing 100 of a three-dimensional image of the brain of the patient, acquired prior to a surgical operation, to obtain a reference cerebral arterial tree structure of the patient, processing 200 of bidimensional images of the brain of the patient, acquired during the operation, to reconstitute at least partially a current cerebral arterial tree structure of the patient, determination 300, from the mapping of the reference and current arterial cerebral tree structures, of a shift field of the vascular tree representing the shift of the current vascular tree relative to the reference vascular tree, application 400 of the determined shift field of the vascular tree to a biomechanical model of the brain of the patient for estimating the global shift of the brain of the patient; this model serves as mechanical interpolator for calculating during the intervention all the volume shifts inside the brain generation 500, from the estimated brain shift of at least one image of the brain of the patient in which the brain shift is compensated.

Determination of the Reference Cerebral Vascular Tree

As described previously, the process comprises a step 100 consisting of processing an image of the brain of the patient acquired prior to the surgical operation. The aim of this processing is to locate the cerebral vascular tree in the image acquired prior to the surgical operation. This cerebral vascular tree in the image acquired prior to the surgical operation corresponds to the vascular tree prior to the brain shift of the patient, and is called hereinafter "reference cerebral vascular tree".

Preferably, the image acquired prior to the surgical operation is a three-dimensional image. More preferably, this three-dimensional image is magnetic resonance angiography.

Magnetic resonance angiography reveals important contrasts between the tissues. Analysis of the magnetic resonance angiography precisely distinguishes the nature of the tissues observed. In particular, the data it contains locate the reference cerebral vascular tree. Also, the acquisition technique of magnetic resonance angiography has the advantage of being non-invasive and therefore of no harm to the patient, contrary for example to techniques emitting ionising radiation, such as tomography.

Once the patient is installed on the operating table, processing of the three-dimensional image to obtain the reference cerebral arterial tree structure comprises an orientation step of the three-dimensional image relative to the head of the patient. In other terms, the spatial position of the reference vascular tree is determined relative to a referential of the physical space of the patient. More precisely, the reference cerebral vascular tree is transposed to the physical referential of the patient, using a technique called rigid recalibration based on the mapping of calibration points with their segmented equivalents in magnetic resonance angiography acquired prior to the operation. Within the scope of the present invention "rigid recalibration" means geometric transformation comprising rotation and translation.

Calculation then finds the transformation between the two systems of coordinates. The calibration points used can be significant anatomical points or surfaces such as the tip of the nose, the superciliary arches, the surface of the cheeks or of the forehead. The calibration points can also be defined by a plurality of adhesive pastilles (at least three and preferably ten) stuck to the skin of the patient prior to acquisition of the magnetic resonance angiography. So, these pastilles are acquired in the angiography at the same time as the brain of the patient.

The radiometric isologues of the calibration points are identifiable in magnetic resonance angiography. Once the patient is installed on the operating table, the surgeon indicates to a location system the position of each calibration point using a sensing device. The location system can be an optical location system (comprising for example a stereoscopic camera), or a magnetic location system, or any other location system known to the person skilled in the art.

Knowing the position of the reference cerebral vascular tree relative to the calibration points, and knowing the position of the calibration points once the patient is installed on the operating table, the system is able to calculate the spatial position of the reference vascular tree relative to the spatial position of the patient. Recalibration between the images and the patient, done at the start of intervention, consequently locates all the elements identified in the image by magnetic resonance in the operating field and, reciprocally, transposes the position of the auxiliaries in the volume of data to follow and control proper execution of the intervention.

Determining the Current Cerebral Vascular Tree

The process also comprises a step 200 consisting of processing a plurality of bidimensional images of the brain of the patient, acquired during the operation, to reconstitute at least partially a cerebral arterial tree structure of the patient called "current cerebral arterial tree structure". During the operation, following a significant brain shift of the patient, the surgeon conducts acquisition of bidimensional images. Within the scope of the present invention "plurality of bidimensional images" means 2D images in a determined volume (three-dimensional) whereof the acquisition planes are secants or parallel. These 2D images can be obtained from any medical acquisition device of 2D or three-dimensional images such as three-dimensional echographic images for example.

These bidimensional images are preferably echographic images acquired in Doppler mode, using a probe located by the location system. The echographic images in Doppler mode display blood flow. Also, the Doppler echography technique has the advantage of being benign for the patient. Pre-operative Doppler echography is therefore a fine tool for exploring brain shifts during intervention. This display mode is based on the Doppler effect and locates, by analysing the variations in frequency of ultrasounds emitted, shifts within tissues, such as blood flow. Segmentation of this type of image is made easier due to colour coding used to represent the velocities of flow. This modality therefore displays in the volume of the encephalon those blood flows which occur along the vascular tree and identifies the position of vessels which irrigate the parenchyma.

Acquisition of bidimensional images is conducted for example as follows. The localised probe is put in contact with the brain of the patient via the craniotomy carried out by the surgeon. A rotation movement is manually imprinted in the localised probe so that the echographic plane scans the part of the brain to the greatest extent possible around the tumour.

The localised probe comprises a marker enabling the location system to define its position and its orientation relative to the physical referential of the patient, and therefore spatially reposition the bidimensional images in the physical referential of the patient. After acquisition of a series of bidimensional images, these are treated to locate the current cerebral vascular tree of the patient. More precisely, the centres of the vessels contained in each bidimensional image are selected to produce a scattergram. This scattergram represents at least partially the current cerebral vascular tree of the patient.

Recalibration of Reference and Current Vascular Trees

In another step 300 of the process, the reference and current vascular tree are mapped to determine a shift field representing the shift of the current vascular tree relative to the reference vascular tree. More specifically, the reference vascular tree is reset relative to the current vascular tree. "Elastic recalibration" means the fact of determining, from sets of data which represent two digital images of the same zone, transformation enabling the reference image to become the current image. In other terms, it is a question of "best" superposing structures contained in two comparable images.

The data coming from the three-dimensional image and the bidimensional images are distinct in nature. On the one hand, the reference vascular tree obtained from the preoperative data is almost continuous, the entire head of the patient is contained in the volume of data, and completed segmentation as such generates no artefacts in the reconstruction of the cerebral vascular tree. On the other hand, the current vascular tree obtained from the peri-operational bidimensional images comprises a scattergram, these bidimensional images cover only a fraction of the volume of the brain. According to the skill of the operator, the bidimensional images can be more or less distributed uniformly in space, some regions comprising multiple acquisitions, while others have no acquisition.

The task of the recalibration step 300 of the cerebral vascular trees is therefore to estimate elastic transformation between:

the current configuration, peri-operational, of the vascular tree defined by a scattered scattergram, redundant, incomplete and noisy, and the reference configuration defined by the complete and proper data obtained from preoperative imaging.

The shift field is then calculated from the correspondence set up between the reference vascular tree and the current vascular tree. Each vector of the shift field has its origin in a point of the reference vascular tree and designates a point of the current vascular tree, deformed.

Elastic recalibration is guided by minimising recalibration energy. This recalibration energy quantifies the similarity between the current vascular tree and the reference vascular tree. Optimal recalibration is attained for zero recalibration energy. The aim of the elastic recalibration step is to iteratively minimise the value of this recalibration energy by having the points of the current vascular tree evolve into the points of the reference vascular tree.

The rapidity of the calculation is obtained by:

prior calculation of a distance map—between each point of the current vascular tree and its counterpart in the radiometric sense (i.e. the point designating the same structure) in the reference vascular tree—on which evaluation of the recalibration energy is based, and determining the direction of stronger descent, calculated at each iteration of the minimisation process.

Given the scattered and irregular nature of the data, the search for an elastic recalibration function must be restricted so as not to end up with aberrant recalibration. The elastic recalibration function is non-linear transformation for moving from the current vascular tree to the reference vascular tree.

More precisely, conditions linked to the nature of the data to be recalibrated are determined to ensure they respect essential physical criteria. With respect to organic data, a first condition to be satisfied by the elastic recalibration function relates to the non-folding of space. In fact, the brain shift of the patient cannot cause folding of the brain of the patient on itself.

A second condition to be satisfied by the elastic recalibration function relates to the continuity of the propagation of the shift. In fact, the reference and current vascular trees are observations of the physical phenomenon of brain shift. Similarly to the process of brain shift of the patient, without tissue tearing or resection, the recalibration function must be continuous and even continuously differentiable i.e. differentiable at any point of the field and having no differential discontinuity.

A third condition to be satisfied by the recalibration function is that two distinct points of the current vascular tree cannot have the same image in the reference vascular tree, and vice versa. The elastic recalibration function such as proposed in the invention has the advantage of being reversible with the preferred degree of precision. Once this recalibration function is calculated, post-processing of the result produced by recalibration eliminates aberrations due to the presence of noise in the data of the bi- or three-dimensional peri-operationals images.

All the shifts of the vascular tree finally retained form a shift field representing the shift of the current vascular tree relative to the reference vascular tree. The reader will appreciate that the recalibration step can be applied to recalibration of structures other than a cerebral vascular tree. In particular, the elastic recalibration presented hereinabove can apply to recalibration of any type of organic tissue.

Extrapolation of the Shift Field of the Cerebral Vascular Tree to the Entire Volume of the Organ by Means of a Biomechanical Model In another step 500 of the process, the determined shift field of the vascular tree is applied to a biomechanical model of the soft tissue of the brain of the patient for estimating the global shift of the brain of the patient. This mathematical model formalises knowledge a priori of the behaviour of the organ and infers therefrom the overall behaviour under constraints of local shift deduced from observation peri-operational, called limited conditions. The biomechanical model (also known under the name of deformable model) plays a double role.

First, the biomechanical model extrapolates the shifts of the vascular tree to the entire volume of the brain to simulate the effect of the brain shift.

Second, the biomechanical model regulates the data. In fact, estimation of the shift field of the vascular tree is tainted by errors due to the imaging mode used, to limitations of segmentation algorithms and to those of calculating elastic recalibration conducted to map the current vascular tree and the reference vascular tree. The biomechanical model harmonises the shift field by deleting the errors in the input data of the biomechanical model. This makes the process resistant to the artefacts present in the noisy data collected during the intervention (i.e. the bi- or three-dimensional echographic images).

The originality of the process relates to the complementarity between a biomechanical model approximating the behaviours of the cerebral tissues of the patient and monitoring of potentially noisy but representative anatomical structure of the brain shift due to the cerebral vascular tree. On completion of step 500 of the process, the global shift of the brain of the patient is estimated.

A final step 600 of the process relates to the generation, from the estimated global shift of the brain, of at least one image of the brain of the patient in which the brain shift is compensated. This image is for example the three-dimensional image (or bidimensional images in section of this three-dimensional image) acquired prior to the operation to which the estimated global shift of the brain of the patient is applied so as to update the preoperative data as a function of the estimated global shift of the brain of the patient.

Verification of the Coherence of the Calculated Shift

Advantageously, the process can comprise a step for the calculation of the disparities between points of the image of the brain generated and one or more bidimensional control images acquired during the operation. This enables the user to verify the coherence and precision of the calculation made by the process described hereinabove. For this to happen, the user can for example acquire one or more bidimensional control images of the brain of the patient to calculate the position error between the points of the bidimensional control images and their isologues in the image generated from the estimated global shift of the brain of the patient.

For example, the user can scan the cerebral tissues in the region of interest while projecting the position of the vascular tree deformed by the model in the bidimensional control images. Superposition of the two data i.e. Doppler in real time obtained by scanning of the organ, on the one hand and simulated Doppler signal, calculated from the incidence of the localised echographic sections relative to the vascular tree deformed by the system, on the other hand, enables the user to evaluate the coincidence between the model and the reality of the patient. The appreciation of the quality of the shift enables the user to take the decision to follow or not follow the indications of the system on the basis of the updated preoperative data.

As the brain shift is an evolutive process, this validation is made as soon as possible after the acquisition of data on which the shift algorithm is based to guarantee its pertinence. The process described hereinabove is superbly adapted to a continuous monitoring of the shift in soft tissue of the brain, as much by its response time of the order of a few seconds as by the repeatability of the data acquisition procedure which needs no major interruption in the intervention or placing of bulky equipment.

Theory Associated with Elastic Recalibration

The theory associated with the elastic recalibration step will now be described in greater detail. The following explanations are given in relation to the elastic recalibration of the cerebral vascular tree, but it is understood that this recalibration can be applied to other types of organic tissue.

Elastic recalibration is an application $R: \mathbb{R}^3 \rightarrow \mathbb{R}^3$, which minimises some recalibration error, or rather energy recalibration defined between a set of source points S and another set of destination points D. The energy of the recalibration R is the measurement of "similarity" between the set of transformed points R(S) and the target set D. When the two sets are combined, this energy becomes zero and recalibration is complete. If the recalibration energy and the function space in which the transformation R evolves are not defined correctly, then the problem consisting of finding an optimal R is poorly put, i.e. the existence and the uniqueness of R are not guaranteed.

In this part we present the scope of calculation of the elastic shift which rigorously sets up elastic correspondence between the data being considered. The specificities of this approach reside in the mathematical properties of the transformation R, shown hereinbelow, which guarantee the physical realism.

Recalibration Energy

The recalibration energy can be freely defined to reflect the nature of the recalibration problem being processed. For example, in the case of recalibration between two images, this measurement can be based on the differences between the values of pixels, or voxels, of the source and destination images. In the present case, the similarity between the sets of data S and D is defined by the spatial proximity of the two scattergrams. With no other knowledge of the nature of the data being handled it is possible for example to define recalibration energy $E_{reg}$ as the average of the minimal Euclidean distances between R(S) and D.

$$E_{reg}(R) = \frac{1}{\text{Card}(S)} \sum_{s \in S} d(R(s), D) + \frac{1}{\text{Card}(D)} \sum_{d \in D} d(d, R(S))$$

Where:
R represents the elastic recalibration function,
Card(S) is the cardinal of the source set S,
Card(D) is the cardinal of the destination set D,
d(R(s),D) represents the distance between the set D and the transform by R from a point s of the set S,
d(d, R(S) represents the distance between a point d of the set D and the transform by R of the set S.

In this case optimal recalibration is conducted when the value of $E_{reg}$ is cancelled. The symmetrical energy presented hereinabove supposes that each structure present in S can find, using appropriate transformation means R, a correspondence among D, and reciprocally. The designations "S" and "D" of the two sets of data are interchangeable.

In the present case, however, the structures present in S and D cannot be equivalent and the hypothesis symmetry does not hold since the structures in S represent only a subset of D. An alternative definition must be found for consideration. From here on, "S" will be used to designate the set of points defining the current configuration, peri-operational, of the vascular tree, and D to designate those which define its preoperative reference configuration. The elastic recalibration function R is therefore the one which leads the points of S on D and an asymmetrical definition of the energy of this recalibration can be formulated by truncating the symmetrical expression hereinabove:

$$E_{reg}(R) = \frac{1}{\text{Card}(S)} \sum_{s \in S} d(R(s), D)$$

The significance of the "source" and "destination" appellations can be better understood by seeing elastic recalibration as an iterative process where the source points S are shifted towards the destination set according to an optimal trajectory on a potential energy surface whereof the relief is defined by the spatial configuration of the points of D. The candidate configuration R(S) is evaluated on the set contained fewer data, whereas the energy function is more strictly defined by D, which contains the reference information on the whole structure of the vascular tree. Alternative solutions to the problem of asymmetry feature in the literature. The definition hereinabove of $E_{reg}$ can result in situations where a group of source points is calibrated to a confined part of D, in other words, this energy does not favour distribution of the source points over the structure destination. To avoid this, it is possible to extend the expression thereof by adding a term which quantifies this distribution but which operates solely in a restrained vicinity of points of D which contain points of R(S).

Finally, given that the cardinal of the set S does not evolve during recalibration, it is still possible to simplify the preceding expression of the energy $E_{reg}$ by eliminating the multiplicative constant which precedes it, which gives the following definition of $E_{reg}$:

$$E_{reg}(R) = \sum_{s \in S} d(R(s), D)$$

Shift Function Space

Given the scattered and irregular nature of the data, the search for an elastic recalibration function must be restricted so as not to end up with aberrant recalibration. This stumbling block is mainly due to the numerous local minima which delimit the product of the energy function for a given configuration D. The two sets S and D are observations of the physical phenomenon studied i.e. the brain shift.

It is therefore supposed that similarly to the process of the "brain-shift", without tearing or resection of tissue, the preferred non-linear transformation R is continuous and even continually differentiable, i.e. differentiable at any point of the field and having no differential discontinuity. This defines a first restriction on the search space of the recalibration functions $R \in C^1(\mathbb{R}^3)$.

Another major restriction on the nature of the transformation is that it must not fold the space. The restriction of non-folding can be expressed mathematically as follows. Let us consider a positively oriented trihedron comprising three infinitesimal vectors, $dX_1$, $dX_2$ and $dX_3$, placed at point p of space. Let dV be the volume, positive, defined by these three vectors and whereof the value is given by the determinant of the matrix formed by the three vectors.

$$dV = (dX_1 \times dX_2) \cdot dX_3 = |dX_1 dX_2 dX_3|$$

After application of the transformation R to the point p the three vectors transform into $dX_1$, $dX_2$ and $dX_3$. The infinitesimal nature of these vectors gives the following approximation:

$$\forall i = 1, 2, 3, \, dx_i = \frac{\partial R}{\partial p}(p) dX_i$$

The volume defined by the transformed trihedron, noted as dv is then obtained similarly.

$$dv = |dx_1 \, dx_2 \, dx_3| = \left|\frac{\partial R}{\partial p}(p)\right| |dX_1 \, dX_2 \, dX_3| = |J_R(p)| dV$$

The restriction of non-folding is mentioned quite simply: dv>0, which signifies that the deformed infinitesimal volume has not been "turned round" (dv<0) by R or totally crushed (dv=0). Thus the application R does not locally fold the space if and only if its Jacobian at p is strictly positive. In our case, elastic recalibration must not fold the space at any point, which gives the expression of the restriction of non-folding:

$$\forall p \in \mathbb{R}^3, |J_R(p)| > 0$$

If at any given point the Jacobian is greater than 1 this means that elastic recalibration locally stretches the volume, and if on the contrary it is less than 1 the volume is contracted. Finally, the product of the Jacobian matrix of R calculated at a point by a unit vector gives the elongation rate or contraction rate of space in a given direction in the vicinity of this point. FIG. 3 shows a shift of a unit square with a folding of space.

Finally, and for the same physical motivations, the application R must be injective. This is translated by the fact that two distinct points cannot have the same image by R and, physically, R must not lead two atoms to the same point in space. If R is an injection, then a predecessor can be calculated for each "attained point" $p \in \text{Image}(R)$.

In the present case where S represents a fraction of the structure present in D, the preferred transformation in fine is that which guides D to S, or $R^{-1}$, in order to define the shift field of the vascular tree of the reference configuration D to the current configuration S, as described hereinabove. For the expression $R^{-1}$ to make sense, it must be that $D \subset \text{Image}(R)$. To simplify these considerations, the one-to-many R functions such as $\text{Image}(R) = \mathbb{R}^3$ are considered. It can therefore be concluded that the preferred recalibration function R is bijective.

The non-folding restriction guarantees that the Jacobian is strictly positive at any point of $\mathbb{R}^3$, though this is insufficient to guarantee the global bijectivity. The function space must be conveniently defined to ensure bijectivity of the function R. The following sections describe the recalibration strategy adopted to result in minimisation of the recalibration energy while respecting the differentiability restrictions mentioned earlier, both non-folding and bijection.

Calculation of Recalibration

The approach presented here is inspired by mechanical modelling of solids based on digitalising of finished elements type. In order to approximate the mechanical behaviour of the non-structured data, it is supposed that the scattergram subjected to the shift is encased in a virtual elastic solid. Since the points shift translates the physical properties of an underlying structure, the geometry of which is unknown, the form of a box encasing points is attributed arbitrarily to this virtual solid. All the admissible shifts are defined as the successive combinations of elementary shifts of the encasing solid, the effects of which spread through its volume and modify the position of the internal points. The elementary shifts mentioned here are defined later. The three-dimensional recalibration technique described here can easily be derived in a 2D recalibration technique by replacing the notion of "virtual solid" by "virtual plane". The illustrations presented hereinbelow are based on 2D implementation of recalibration to clarify its concepts.

The elastic recalibration function is assembled iteratively such that the recalibration energy $E_{reg}$ optimally diminishes at each step. Let $S_0 := S$, the initial source scattergram, and let $S_1$ be the source scattergram obtained following the iteration i. The field of the virtual solid is digitalised with a certain level of refinement in regular hexaedres (or squares, in 2D) called "cells". The elementary shifts of the solid are obtained by individually shifting the nodes of the resulting grille.

The union of cells enclosing a node n defines its "vicinity", noted as V (n). An elementary recalibration function r is defined by spreading the shift of the node n to the set of points $\mathbb{R}^3$ under the following restrictions:

$$\begin{cases} \text{The boundary of the vicinity of } {}^{n,\partial V(n)} \text{ is unchanged i.e.}^{i.e. \forall p \in \partial V(n), r(p) = p}; \\ \text{The vicinity of the } n \text{ rest is overall unchanged i.e.}^{r(V(n)) = V(n)} \end{cases}$$

All the points outside this vicinity remain unchanged i.e. $\forall p \notin V(n), r(p) = p$.

Each node of the digitalised solid is considered and the gradient of the recalibration energy, as a function of the shift of the node, is calculated. The opposite of this vector defines the preferential shift of the node, that is, that which when applied to the node causes the biggest drop in recalibration energy. Of all the nodes, the one which allows the biggest drop in gradient is selected and its preferential shift is applied to it, whereas the other nodes remain immobile. The local shift of the solid is calculated by spreading the shift of the node via its vicinity and the position of the source points it contains is modified as a consequence, giving the new configuration of the scattergram Si+1.

Once the elementary shift is applied, the solid returns to its initial configuration, at rest, and the source points Si+1 are distributed in its volume. A new iteration can then be calculated by taking the new configuration Si+1 as the starting point. The iterations finally stop when no significant drop in energy can be obtained by shifting the nodes of the grille of the solid.

The iterative loop described hereinabove supposes a degree of refinement of the fixed field Ω. A multi-scale approach was adopted to maintain the spatial consistency of S during assembly of R and avoid its fragmentation. The iterative assembly of R starts at the coarsest level of refinement and when the recalibration energy cannot be more improved at a given level the cells are subdivided into 8 sub-cells (or 4, in 2D) as for an octree. The refinement iterations stop when the maximal degree of subdivision specified manually has been reached. The dimension of the smallest cell attained during the refinement process defines the dimensions of the smallest structure present in S and which will not be recalibrated correctly if an equivalent structure is absent from D:

FIG. 4 illustrates in 2D the iterative multi-scale approach described above. The source points S are represented by reference points 1. The set D is not represented, for the sake of clarity. At (a) the initial set S0:=S is placed inside the virtual solid (reference 2) digitalised by a cell (level 1) and the gradients of the energy recalibration are calculated at its four nodes 3. At (b) the best nodal shift is applied to the solid and the source points are moved to S1. (reference 4). The solid returns to its initial configuration (a). After several iterations, if no significant improvement in energy can be obtained, the level of refinement of the grille increases (c). The energy gradients are calculated at nine nodes 5 of the new grille. At (d) the best shift is applied to the solid and the new configuration of source points S2 (reference 6) is calculated.

Because of the "reset to zero" technique of the shift of the solid after each iteration, major shifts of S are feasible without having to maintain an irregular grille, subjected to a sum of important shifts which would have been the case if the solid strictly followed the shifts of S. The regularity of the grille prior to each iteration also allows a substantial gain in calculatory effort, given that interpolation of nodal shifts can be calculated on the basis of a cell of cubic type. Before more detail on the calculation of R is given, we must extend the intuitive concept of the virtual solid so that each elementary shift is defined as an application $\mathbb{R}^3 \to \mathbb{R}^3$. so as to respond to the restriction mentioned earlier.

For this we will consider a source point placed at the boundary of the virtual solid ∂Ω, for example near the upper edge of the square in FIG. 4. If the node is shifted as is illustrated at (d), this point will fall outside the solid in its rest configuration (square) and will become a "dead point" the position of which could not be modified by the following iterations which have an effect only on the Ω cells.

To eliminate this disadvantage a margin of cells of dimensions identical to those used for the digitalising is added around the field. This addition is made at each level of refinement. The outer nodes of these cells are fixed and ensure an interface role between the deformable zone and the rest of $\mathbb{R}^3$ which remains unchanged. FIG. 5 shows the supplementary cells 7 inserted at the margin of the digitalising of the field for two successive levels of refinement.

Properties of Elastic Recalibration

Let $G1, \ldots, GJ$ be the successive levels of refinement, $G1$ being the coarsest level and $GJ$ the finest. Let $\{r_j^i: \mathbb{R}^3 \to \mathbb{R}^3, i \in [[1, I_j]]\}$ be the set of elementary shifts calculated at each level of refinement j (where lj is the total number of elementary shifts at level j). The expression of the elastic recalibration function R assembled iteratively is:

$$R: p \mapsto \left( \underbrace{r_J^{l_J} \circ \ldots \circ r_J^1}_{G_J} \circ \ldots \circ \underbrace{r_1^{l_1} \circ \ldots \circ r_1^1}_{G_1} \right)(p)$$

It is clear that the properties of differentiability, non-folding and bijection of R depend on the properties of the elementary recalibration functions $r_j^i$. If each $r_j^i$ is a $\mathbb{R}^3 \to \mathbb{R}^3$ bijection then the recalibration function R is also a bijection and its inverse is given by:

$$R^{-1}: p \mapsto \left( \underbrace{r_1^{1-1} \circ \ldots \circ r_1^{l_1-1}}_{G_1} \circ \ldots \circ \underbrace{r_J^{1-1} \circ \ldots \circ r_J^{l_J-1}}_{G_J} \right)(p)$$

If each $r_j^i$ is a continuously differentiable application $\mathbb{R}^3 \to \mathbb{R}^3$ then the recalibration function R is one also. Let $p_0 \in \mathbb{R}^3$ be any point and pk the transformed point after application of k elementary shifts. Let $K = I1 + I2 + \ldots +$ then $\{p_k, k \in [[1, K]]\}$ the set of all the successive positions of p0 and $R(p) = pK$. The differential of R at p0 is given by the following composition rule:

$$J_R(p_0) = \frac{\partial R}{\partial p}(p_0) = \frac{\partial r_J^{l_J}}{\partial p}(p_{K-1}) \ldots \frac{\partial r_1^2}{\partial p}(p_1) \frac{\partial r_1^1}{\partial p}(p_0)$$

Finally, if all the $r_j^i$ verify the condition of non-folding, then that is also true of the application R. This is the consequence of the expression of the Jacobian of R:

$$|J_R| = \left| \frac{\partial R}{\partial p} \right| = \prod_{j=1 \ldots J} \prod_{i=1 \ldots l_j} \left| \frac{\partial r_j^i}{\partial p} \right| = \prod_{j=1 \ldots J} \prod_{i=1 \ldots l_j} |J_{r_j^i}|$$

Thus, to prove that any function R of the family of elastic recalibration functions generated using the procedure described above verifies the restrictions of differentiability, bijection and non-folding, it suffices to prove that these properties are verified for each of the elementary recalibration functions $r_j^i$ which comprise R.

Study of Elementary Recalibration Functions

General Expression of $r_j^i$

At this point, the family of elementary recalibration functions must be specified. In the Finished Elements method, a nodal value (shift or other quantity) is interpolated via the digitalised volume by way of functions of form $w: \mathbb{R}^3 \to [0, 1]$. The value of the function of form associated with a node and evaluated at a point of the field gives the proportion of the nodal value transferred at this point. Thus, the value of w at its node is 1. The same mechanism for spreading the shift of a node through its vicinity will be used.

The $n^{th}$ iteration recalibration conducted at the level of refinement j and using the elementary recalibration function is considered. The indices of order and level of refinement i and j will be omitted throughout this paragraph. Let $\vec{u}$ be the shift and w be the function of form associated with the node whereof the shift is made during this iteration.

The expression of r is therefore:

$$r: \mathbb{R}^3 \to \mathbb{R}^3, p \mapsto p + w(p)\vec{u}$$

The conditions on the zone of influence of r translate by restrictions on the support of w as follows:

$$\begin{cases} \forall p \in \partial V(n), r(p) = p \Rightarrow w(p) = 0 \\ \forall p \notin V(n), r(p) = p \Rightarrow w(p) = 0 \end{cases}$$

Note that the support of w is $\text{supp}(w) = V(n)$ which is a compact $\mathbb{R}^3$ Differentiability The differentiability of r flows from that of $w: \mathbb{R}^3 \to [0, 1] \in C^1(\mathbb{R}^3)$, so $r \in C^1(\mathbb{R}^3)$ and the Jacobian matrix of r is written as:

$$\frac{\partial r}{\partial p} = Id_{3 \times 3} + \begin{pmatrix} u_x \\ u_y \\ u_z \end{pmatrix} \begin{pmatrix} \frac{\partial w}{\partial x} & \frac{\partial w}{\partial y} & \frac{\partial w}{\partial z} \end{pmatrix}$$

$$= \begin{pmatrix} 1 + u_x \frac{\partial w}{\partial x} & u_x \frac{\partial w}{\partial y} & u_x \frac{\partial w}{\partial z} \\ u_y \frac{\partial w}{\partial x} & 1 + u_y \frac{\partial w}{\partial y} & u_y \frac{\partial w}{\partial z} \\ u_z \frac{\partial w}{\partial x} & u_z \frac{\partial w}{\partial y} & 1 + u_z \frac{\partial w}{\partial z} \end{pmatrix}$$

where $Id_{3 \times 3}$ is the identity matrix 3×3.

So that r can be $C^1(\mathbb{R}^3)$ it suffices for w to be it also.

Non-Folding

In rewriting the non-folding restriction using the expression of the Jacobian matrix of r and by developing the determinant of the matrix produces a new expression of the restriction of non-folding:

$$\forall p \in \mathbb{R}^3, 1 + \vec{\nabla} w(p) \cdot \vec{u} > 0$$

Since $p \mathbb{R} \|\vec{\nabla} w(p)\|$, is a continuous application with compact support, let $p_{max} \in \mathbb{R}^3$ be the point where $\|\vec{\nabla} w\|$ attains its maximum $M := \|\vec{\nabla} w(p_{max})\|$, $M > 0$.

Then the preceding equation is equivalent to:

$$\|\vec{u}\| < \frac{1}{M}$$

The non-folding of r can therefore be guaranteed by limiting the amplitude of the nodal shifts. The maximal norm of the shift nodal is given by the inverse of the maximal norm of the gradient of the function of form considered w.

Bijection

Let $V := V(n)$ the closed union of cells enclosing the node n. In this part it will be shown that if an elementary application r does not fold the space, then it is also bijective of V in itself, but also of R3!R3, since the points outside V are not affected by r.

Implementation

Choice of an Expression of w

To simplify calculation of the elastic recalibration, a polynomial expression of w is selected. Let $\pi$ be a polynomial of degree 3, defined by:

$$\begin{cases} \pi(0) = 0 \\ \pi(1) = 1 \\ \pi'(0) = 0 \\ \pi'(1) = 0 \end{cases}$$

Its expression is $\pi(t)=t^2(3-2t)$.

A function of form w defined on the "canonic" cell $[0,1]^3$ and taking the value 1 to the node $n=(1, 1, 1)^T$ can be obtained as:

$$w(p)=w(p_1,p_2,p_3):=\pi(p_1)\pi(p_2)\pi(p_3).$$

FIG. 6a shows the function of form restricted to a dimension, i.e. $w=\pi$ on the interval $[0, 1]$. The function of form w is defined on the union of adjacent cells around the node n by a change in variable and scaling to adapt its field of canonic definition $[0,1]^3$ to the dimensions of the cells in the digitalising grille of the virtual solid. FIG. 6b shows the changes in variable necessary for assembling from the canonic function of form, the function of form w on a vicinity of 2×2 cells of the plane. FIG. 6c shows the trace of the resulting function of form w: $\mathbb{R}^2 \to \mathbb{R}$ Non-Folding and Bijection Restriction After the expression of w has been selected, it is possible to calculate the amplitude of the maximal nodal shift authorised for a function of elementary recalibration r. An upper limit M is calculated for the quantity $\|\vec{\nabla}w\|_1$ to define this amplitude, on the field $[0,1]^3$.

The derivative of $\pi$ est $\pi'(t)=6t(1-t)$. It attains its maximum on $[0, 1]$ at tmax=½ where $\pi'(t_{max})=3/2$. The $\vec{\nabla}$w: expression is obtained $$\vec{\nabla}\omega(p) = \begin{pmatrix} \pi'(p_1)\pi(p_2)\pi(p_3) \\ \pi(p_1)\pi'(p_2)\pi(p_3) \\ \pi(p_1)\pi(p_2)\pi'(p_3) \end{pmatrix}$$

On $[0,1]^3$ there is $$(\pi'(p_1)\pi(p_2)\pi(p_3))^2 \leq \left(\frac{3}{2}*1*1\right)^2 = \left(\frac{3}{2}\right)^2$$

This upper boundary is valid for each coordinate, so $$\|\vec{\nabla}\omega\| \leq \sqrt{3\left(\frac{3}{2}\right)^2} \text{ and thus } \|\vec{\nabla}\omega\| \leq \frac{3}{2}\sqrt{3}.$$

Given this upper limit for the norm of the gradient, a sufficient condition which guarantees bijection and similarly the non-folding of space for functions of elementary shift defined for a canonic grille comprising cells $[0, 1]$ is therefore $$\|\vec{u}\| \leq 0.38 < \frac{2}{3\sqrt{3}}.$$

This result can be extended to any dimension of cell as follows: Let Cell:=$[\alpha,\alpha+L]\times[\beta,\beta+L]\times[\gamma,\gamma+L]$ be a cubic stop cell L. Let $\phi$ be the $\mathbb{R}^3 \to \mathbb{R}^3$ function which transforms this cell into a canonic cell $[0,1]^3$ defined by:

$$\phi(p_1,p_2,p_3):=(\phi_1(p_1),\phi_2(p_2),\phi_3(p_3))=((p_1-\alpha)/L,(p_2-\beta)/L,(p_3-\gamma)/L).$$

The function of form w defined on Cell is $w(p)=w(p_1, p_2, p_3)=\pi(\phi_1(p_1))\pi(\phi_2(p_2))\pi(\phi_3(p_3))$ and:

$$\vec{\nabla}\omega(p) = \begin{pmatrix} \frac{1}{L}\pi'(\varphi_1(p_1))\pi(\varphi_2(p_2))\pi(\varphi_3(p_3)) \\ \pi'(\varphi_1(p_1))\frac{1}{L}\pi'(\varphi_2(p_2))\pi(\varphi_3(p_3)) \\ \pi(\varphi_1(p_1))\pi(\varphi_2(p_2))\frac{1}{L}\pi'(\varphi_3(p_3)) \end{pmatrix}$$

In the same way as for the canonic cell, it can be concluded that an upper limit for the norm of the gradient is:

$$\|\vec{\nabla}\omega\| \leq \frac{3}{2L}\sqrt{3}$$

This leads to the sufficient condition guaranteeing for a cell of dimension L the bijection and the non-folding of the shift elastic elementary r:

$$\|\vec{u}\| \leq 0.38L$$

Given that the approach presented here is based on mechanical modelling of solids, the choice is made to restrict the amplitude of the individual shifts of the nodes to the field called "small shifts". For this to happen, the amplitudes of the shifts imposed on the cells of the solid are limited to 10% of their dimension, or:

$$\|\vec{u}\| \leq 10\% L$$

A consequence of this restriction is that the compression and stretching of space applied to the solid at each iteration are terminals. Since $\|\vec{u}\| \leq L/10$ and $\|\vec{\nabla}w(p)\| \leq (3\sqrt{3})/(2L)$, then:

$$1 - \frac{3\sqrt{3}}{20} \leq 1 + \vec{\nabla}\omega(p) \cdot \leq 1 + \frac{3\sqrt{3}}{20}$$

The equation hereinabove provides an approximation (($3\sqrt{3})/20\cong 0.25980\ldots$) of the lower and upper terminals of the Jacobian of r valid for all dimensions of cells:

$$\forall p \in \text{Cell}, 0.74 < |J_r(p)| < 1.26$$

Minimisation of Energy

Two sets S and D having the cardinals nS=Card(S) and nD=Card(D) are considered. Minimisation of the recalibration energy $E_{reg}$ requires calculation of the minimal distance between each point of S and the set D. The complexity of the raw calculation, considering for each point of S its distance at each point of D is s is nS×nD. Numerous techniques have been proposed for accelerating calculation of the nearest distance between two sets of points, mainly within the scope of rigid recalibration based on the principle of ICP for "Iterative Closest Point".

To accelerate the calculation of $E_{reg}$ at each iteration, a Euclidian distance map is calculated from the points of D. The distance map is calculated on a three-dimensional grille discretising the space around D. On each node of the grille gi, the minimal distance to D, d(gi,D) is memorised. This structure of data is initialised at the pre-operatory phase, right after the segmentation of the vascular tree D in the MRA images.

The content of the distance map is then registered in the form of a binary file to be read at the start of intervention by the system, before any elastic recalibration calculation. For a given source point s, the value of d(s,D) is calculated by trilinear interpolation among the 8 values read in the grille of the distance map, associated with the apexes which surround s, $\{gi\}i=s1, \ldots, s8$. During recalibration, at each iteration, the best shift for each node of the grille which digitalises the virtual solid is calculated using the gradient of $E_{reg}$.

Calculation of the shift nodal is carried out in two steps:
1. The gradient of $E_{reg}$ relative to the nodal shifts is estimated by finished differences;
2. A search along the direction of strongest descent is conducted to estimate the optimal step;
3. The amplitude of the resulting shift is limited to satisfy a restriction. Given that only those shifts from a node at the same time, n, are considered only the three coordinates of the nodal shift vector $\vec{u}$ are involved in the minimisation calculation. The minimised function is $f: \mathbb{R}^3 \to \mathbb{R}$ defined by:

$$f(\vec{u}) = E_{reg}(r \circ R)$$

Where $r: p\mathbb{R} \; p+w(p)\vec{u}$ is the elementary recalibration function associated with the node n, and R is the overall recalibration function assembled prior to the current iteration.

The strategy consisting of returning to the initial form of the virtual solid on completion of each iteration supposes that the set of source points at the outset of iteration has already been transformed by R according to the algorithm described hereinabove, allowing us to leave aside the background of the recalibration constituted by R.

Let $\{s^i\}_{i \in I} \subset S$ be the set of source points the position which belongs to the support of the function of form w associated with the meshing node n. Since these are the only points concerned by the shift of n at the current iteration recalibration, calculation of the recalibration energy can be restricted to this set. This allows us to express the function f to be minimised as:

$$f(\vec{u}) = E_{reg}(r) = \sum_{i \in I} d(r(s^i), D)$$

The function f is not systematically differentiable relative to $\vec{u}$, due to the square root borne by the distance, and the operator min(x, y) operating on the distances between the scattergrams. The direction of greatest descent must therefore be estimated locally by finished centred differences. This results in:

$$\forall k = 1, 2, 3, \; \frac{\partial f}{\partial u_k}(\vec{0}) \approx \frac{F(\epsilon \vec{e_k}) - f(-\epsilon \vec{e_k})}{2\epsilon}$$

where $\in$ is a very small value relative to the maximal amplitude of the possible shift of n, which is less than 10% of the size of the cell L, giving $\in \ll L/10$.

The vectors $\{\vec{e_k}\}_{k=1,2,3}$ form the canonic basis of $\mathbb{R}^3$. The vector of greatest descent on f can be written as:

$$-\vec{\nabla}f = -\left(\frac{\partial f}{\partial u_1}(\vec{0}), \frac{\partial f}{\partial u_2}(\vec{0}), \frac{\partial f}{\partial u_3}(\vec{0})\right)^T$$

The length of the maximal step authorised by the non-folding restriction is 10% of L, which defines the maximal shift vector of the node n in the direction of descent on f:

$$\vec{u}_{max} = -\frac{L}{10}\frac{\vec{\nabla}f}{\|\vec{\nabla}f\|}$$

The best nodal shift in the sense of minimisation of the recalibration energy therefore corresponds to the minimum of the function $f(\vec{0} + t\vec{u}_{max}) = f(t\vec{u}_{max})$ for $t \in [0, 1]$.

An appropriate estimation of this minimum is obtained by approximating on the interval [0, 1] the function $t\mathbb{R} \; f(t\vec{u}_{max})$ by a parabola $P: t\mathbb{R} \; At^2 + Bt + C$ The three coefficients of the parabola A, B and C are determined by local information on the behaviour of f and evaluation of its value at maximal step: $f(\vec{u}_{max})$ Thus:

$$\begin{cases} P(0) = C = f(\vec{0}) \\ P'(0) = B = \vec{\nabla}f \cdot \vec{u}_{max} = -L/10\|\vec{\nabla}f\| \\ P(1) = A + B + C = f(\vec{u}_{max}) \Rightarrow A = f(\vec{u}_{max}) + L/10\|\vec{\nabla}f\| - f(\vec{0}) \end{cases}$$

Two situations are possible. If A>0 then P is a convex parabola and its minimum is attained at tmin=-B/(2A). In this case, if tmin>1 then the value of the step is limited to 1. If on the contrary, A<0 then P is a concave parabola and its minimum is attained at tmin=1.

Figure 7:
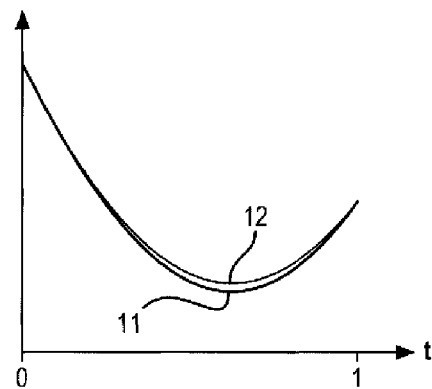
FIG. 7 illustrates an example of approximation of a recalibration energy curve via a parabola.

FIG. 7 shows a representative example of approximation of the energy recalibration curve 11 by a parabola P 12 on the interval [0, 1]. Spread measurements between the two curves, taken over a large number of sets of data during execution of the recalibration procedure, shows the qualities of this approximation. The curve of the bottom 11 is obtained by sampling the recalibration energy on the interval [0, 1], while that of the top 12 is the trace of the parabola P. Despite a slight spread between the values of the two curves, it is evident that the values of t for which these curves attain their minimum are almost identical. For a given level of digitalising refinement of the virtual solid, minimisation of the energy is guided step by step to no significant decrease can be obtained by application of a shift to one of the meshing nodes. In this case, if the maximal level of refinement has not been attained, the grille is improved and the same procedure is repeated.

Inversion

Calculation of the inverse of the elastic recalibration function $R^{-1}$ will now be described. This calculation needs successive inversion of all the elementary recalibration functions: $(r_j^i)^{-1}$. Given that no analytical expression can be given for $(r_j^i)^{-1}$ calculation of $(r_j^i)^{-1}(q)$ is individually completed for each point q considered. To simplify the writing, the indices i and j will not be specified hereinafter, and an elementary function r, associated with the shift $\vec{u}$ of the node n, will be considered more generally.

For a given point $q \in V(n)$, its antecedent $p = r-1(q)$ is calculated as follows. It has been seen previously that p can be written as $p = q + t_p\vec{u}$ where tp is the root of the polynomial function f on the interval [ta, tb]. In fact, since $0 \leq w(p) \leq 1$ the search interval can be restricted to [max{-1, ta}, 0].

The choice of expression of the function of form $w(p_1, p_2, p_3)=\pi(p_1)\pi(p_2)\pi(p_3)$ leads to the following expression of f:

$$f: t \mapsto \mathbb{R} \; t + \pi(q_1+tu_1)\pi(q_2+tu_2)\pi(q_3+tu_3)$$

π is a polynomial of degree 3 at t, therefore f is of degree 9. Since there is no explicit formula for finding the roots of a polynomial of degree 9; an iterative technique of Newton type must be employed.

Assuming that the value of ta is already initialised at max{-1, ta}, the start point is estimation of the following solution:

$$t_p^0 := t_a - \frac{f(t_a)}{f(0)-f(t_a)}(0-t_a)$$

The iterations are then completed conventionally:

$$t_p^{i+1} = t_p^i - \frac{f(t_p^i)}{f'(t_p^i)}$$

The approximation of $r^{-1}(q)$ at each iteration is given by $p^i := q + t_p^i \vec{u}$ and the corresponding error in deformed space is $\|r(p^i)-q\| = |f(t_p^i)| \|\vec{u}\|$.

The precision of the approximation of the inverse is measured in the initial space, not deformed, by evaluating the quantity $\|p^i-p\|$. p is not known, which makes the evaluation of this error difficult. In order to evaluate $\|p^i-p\|$, it is taken into consideration that the inverse application $r^{-1}$ is k-Lipschitzian, in other words:

$$\exists k > 0, \forall p,q \in \mathbb{R}^3, \|r^{-1}(p)-r^{-1}(q)\| \le k\|p-q\|$$

This property then increases the error $\|p^i-p\|$ by:

$$\|p^i-p\| = \|r^{-1}(r(p^i))-r^{-1}(q)\| \le k\|r(p^i)-q\| = k|f(t_p^i)|\|\vec{u}\|$$

The iterations of the Newton algorithm are to be continued until the preferred precision is achieved i.e. when $\|p^i-p\| \le \in$. In light of this, this stop condition is verified when $|f(t_p^i)| \le \in / (k\|\vec{u}\|)$. This inequality constitutes a reliable stop criterion defined in the non-deformed space.

Figure 8:
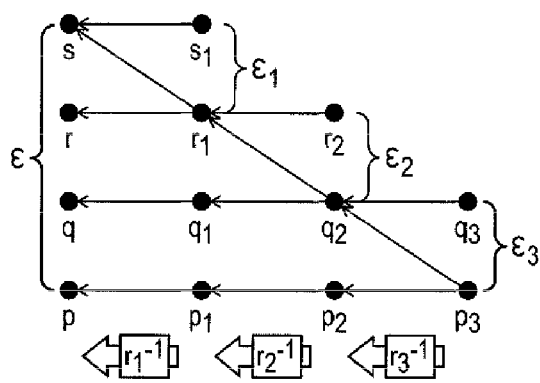
FIG. 8 illustrates three steps of the approximation of the inverse of the recalibration function.

The case of recalibration function R composed of several elementary functions rj is now considered. In this case, precision of the calculation of the inverse R−1 must be controlled at each step of inversion $r_j^{-1}$ of an elementary function. It is clear how the precision of the calculation of R−1 can be evaluated using Lipschitz constants of the functions $r_3^{-1}$.
For the sake of clarity it is supposed that $R = r_3 \circ r_2 \circ r_1$
The aim is to evaluate $R^{-1} = r_1^{-1} \circ r_2^{-1} \circ r_3^{-1}$, by having for each of the $r_3^{-1}$ a Lipschitz constant kj.
Let $p \in \mathbb{R}^3$ be the preferred antecedent of $p3=R(p)$ having intermediate images $p1=r1(p)$ et $p2=r2(r1(p))=r2(p1)$. FIG. 8 illustrates, from right to left, the three steps of the approximation $R^{-1}(p_3)$ as well as the successive accumulation of errors committed at each step:
1. q2 approximates $p_2 = r_3^{-1}(p_3)$ The error in the deformed space is __3:=kq3−p3k. This error spreads to the non-deformed space as $\in_3 k_3$, $\in_3 k_3 k_2$ and finally $\|q-p\| \le \in_3 k_3 k_2 k_1$.
2. r1 approximates $q_1 = r_2^{-1}(q_2)$ with an error in the deformed space $\in_2 := \|r_2-q_2\|$.
This error propagates to the left, i.e. to the non-deformed space, as $\in_2 k_2$, then $\|r-q\| \le \in_2 k_2 k_1$.
3. Finally, s approximates $r=r_1^{-1}(r_1)$ an error in the deformed space of $\in_1 := \|s_1-r_1\|$. This error propagates as $\|s-r\| \le \in_1 k_1$.
The final error can be increased by the sum of the propagated errors:

$$\in = \|s-p\| \le \|s-r\| + \|r-q\| + \|q-p\| \le \in_1 k_1 + \in_2 k_2 k_1 + \in_3 k_3 k_2 k_1$$

The expression hereinabove can be immediately extended to any elastic recalibration function R. If R comprises N elementary functions and the preferred precision in the non-deformed space is ∈ then the approximation effort can be distributed over the N elementary functions by adjusting the precision threshold of the Newton inversion to:

$$\forall j = 1, \ldots, N \; \epsilon_j = \frac{\epsilon}{N \prod_{i=1}^{j} k_i}$$

where each Lipschitz constant ki must be evaluated once only given that it depends only on the amplitude of the shift applied to the node associated with the elementary function ri and of the size of the cell at the level of refinement in question.

Filtering of Elastic Recalibration and Calculation of the Shift Field

As described hereinabove, the peri-operationals images are noisy and the elastic recalibration can occasionally produce recalibration artefacts. It is accordingly important to put in place a strategy for reducing the number of associations between erroneous source points and destination points, each of its associations translating thereafter by a shift, their effect risks propagating as far as calculation of the biomechanical shift of the model resulting in a considerable loss of precision.

A robust and simple technique has therefore been implemented to eliminate coarse recalibration errors due to the presence of false vessels in the data originating from segmentation. This method is divided into two phases: direct filtering, based on calculation of the recalibration function R, monitoring by inverse filtering, which uses the inverse of the recalibration: $R^{-1}$.

The role of filtering is to eliminate the associations of points which do not verify a given precision criterion. Let dmax be the maximal acceptable distance between a source point and its counterpart at D. Direct filtering eliminates the points of S which do not fulfil the condition $d(R(s),D)<dmax$. The filtered set of source points is $S^f$, defined by:

$$S^f := \{s \in S | d(R(s),D) < d_{max}\}$$

Figure 9:
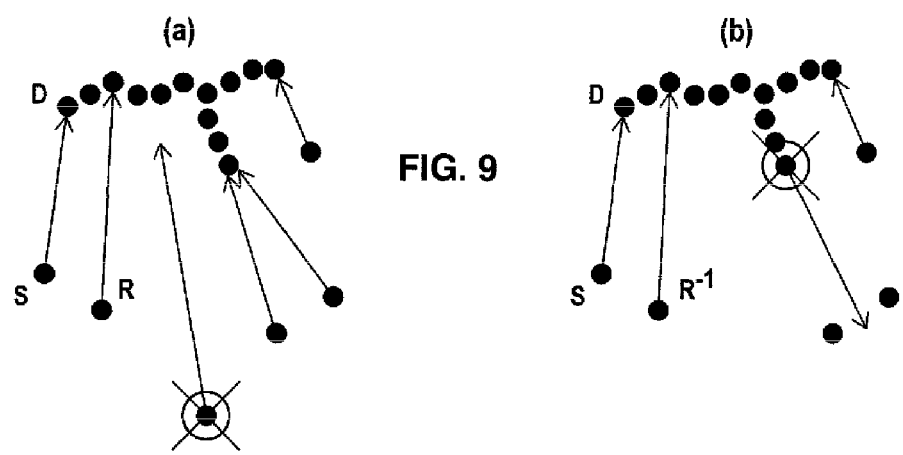
FIG. 9 illustrates direct and indirect filtering steps.

FIG. 9a illustrates the direct filtering step. As is evident in this figure, the source points not yet attained D are eliminated.

The aim of the recalibration procedure is to generate a shift field corresponding to the shift of the structure of the vascular tree (in the presentation given here, but more generally of the shifted organic tissues) defined from preoperative images by D, and which lead them to the current configuration S, obtained by analysis of peri-operational US Doppler images. Inverse filtering verifies that the shift field obtained by inversion of the recalibration function R effectively transforms the points of D into S. So as not to consider the source points eliminated previously, the set S is restricted to $S^f$ and the filtered set of destination points $D^b$ is defined by:

$$D^b := \{d \in D | d(R^{-1}(d), S^f) < d_{max}\}$$

FIG. 9b illustrates the step of inverse filtering. As this figure illustrates, the shifts of D which do not attain S are eliminated.

Finally, the set of shifts of the vascular tree, from its reference configuration to its current configuration, is assembled based on this latter set of points. The shift field intended for the biomechanical model is given by:

$$Disp := \{\vec{u} = \vec{ab}, a \in D^b, b = R^{-1}(a)\}$$

The elastic recalibration described in detail hereinabove constructs an association between two observations of the preand peri-operational cerebral vascular tree, of highly distinct natures. Calculation is guided by minimising of the recalibration energy which quantifies the similarity between the two structures. As optimal recalibration is attained for zero energy, the aim of the recalibration algorithm is to iteratively minimise the value by having the current structure, called "source", evolve into the reference structure, called "destination".

The rapidity of the calculation is obtained by previous calculation of a distance map on which evaluation of the recalibration energy and determination of the direction of greatest descent are based, calculated at each iteration of the minimisation process. The mathematical properties of the recalibration function family engendered by the method described hereinabove guarantee the respect of essential physical criteria, such as non-folding of space, non-covering of material and continuity of propagation of the shift. This elastic recalibration also has the advantage of being reversible with the preferred degree of precision.

Based on the latter characteristic, post-processing of the result produced by recalibration is proposed. This post-processing eliminates aberrations due to the presence of noise in the peri-operational imaging data. The retained set of shifts of the vascular tree finally constitutes the input datum of the biomechanical model the purpose of which is to extend the range to the entire volume of the brain of the patient to simulate the effect of the brain-shift.

Figure 2:
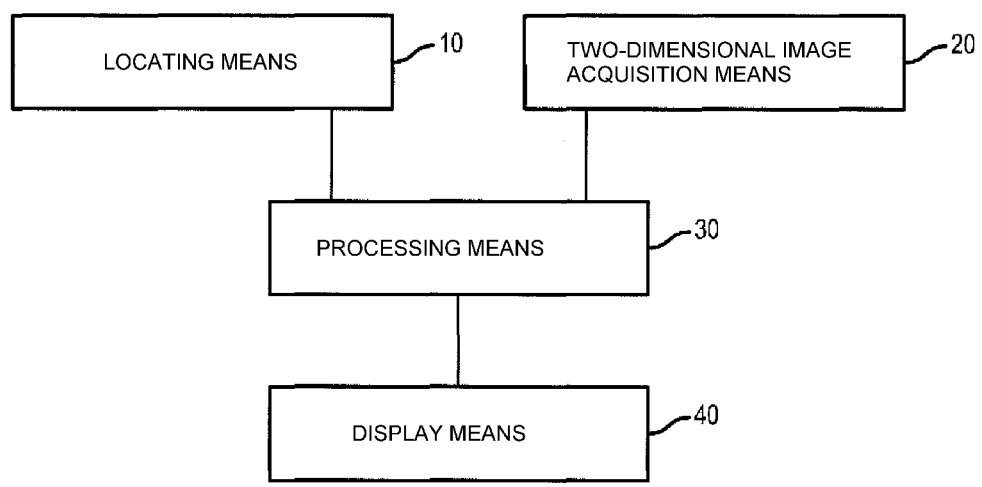
FIG. 2 illustrates an embodiment of the system for executing the process according to the invention.

FIG. 2 illustrates an embodiment of the system for carrying out the process described hereinabove. The system comprises location means 10, acquisition means 20, processing means 30 and display means 40.

The location means locate instruments in space used by the user during the surgical operation. These location means can comprise for example a stereoscopic camera and markers associated with the different objects to be located. The location means 10 also locate in space the head of the patient during intervention, especially for the spatial repositioning of the reference vascular tree calculated from the magnetic resonance angiography.

The acquisition means 20 allow acquisition of bidimensional images during the operation. These acquisition means 20 comprise for example an ultrasound probe localisable by the location means 10. The display means display for example updated preoperative data. These display means can comprise a screen.

The processing means carry out the different calculation steps of the process, and especially:
the processing step 100 of the three-dimensional image of the brain of the patient, acquired prior to a surgical operation, to obtain a reference cerebral arterial tree structure of the patient,
the processing step 200 of the bidimensional images of the brain of the patient, acquired during the operation, to reconstitute at least partially the current cerebral arterial tree structure of the patient,
the step of determining 300, from mapping of the reference and current tree structures arterial cerebral, of the shift field of the vascular tree representing the shift of the current vascular tree relative to the reference vascular tree, and
the application 400 of the determined shift field of the vascular tree to a biomechanical model of the brain of the patient for estimating the brain shift of the patient.

These processing means can be a computer and comprise control means for the control of different material elements of the system.

The person skilled in the art will have understood that numerous modifications can be made to the process described without departing in material terms from the novel ideas presented here. In particular, the recalibration process described previously in relation to recalibration of the cerebral vascular tree can be conducted to enable recalibration of any type of organic tissue which has undergone a shift. Also, even if this recalibration step has been presented in relation to sets of source S and destinations D points of distinct nature due to the difference between the data-recovery zones data or the presence of noise, the recalibration step can be carried out on homogeneous sets of data S and D. It is therefore evident that the examples just given are only particular illustrations and in any case limiting.

The invention claimed is:

1. An image-processing method for estimating a brain shift of a patient, the method comprising:
processing a three-dimensional image of a brain of the patient, acquired prior to a surgical operation, to obtain a reference cerebral arterial tree structure of the patient;
processing bidimensional images of the brain of the patient, acquired during the operation in a determined volume along secant or parallel acquisition planes, comprising selecting centers of vessels contained in each bidimensional image to produce a scattergram and using the scattergram to reconstitute at least partially a current cerebral arterial tree structure of the patient;
determining, from mapping of the reference and current cerebral arterial tree structures, a shift field of a vascular tree representing a shift of a current vascular tree relative to a reference vascular tree;
applying the determined shift field of the vascular tree to a biomechanical model of the brain of the patient for estimating the brain shift of the patient; and
generating, from the estimated brain shift, at least one image of the brain of the patient in which the brain shift is compensated.

2. The method of claim 1, further comprising calculating disparities between generated points of the compensated image of the brain and one or more bidimensional control images acquired during the surgical operation.

3. The method of claim 1, wherein the three-dimensional image acquired prior to the surgical operation includes a magnetic resonance angiography image.

4. The method of claim 1, wherein the bidimensional images acquired during the surgical operation include ultrasound images in Doppler mode.

5. The method of claim 1, wherein the processing of the three-dimensional image to obtain the reference cerebral arterial tree structure comprises orienting the three-dimensional image relative to a head of the patient after installing the latter on an operating table.

6. The method of claim 5, wherein the orienting of the three-dimensional image comprises:
locating a set of calibration points on the head of the patient after installing the latter on the operating table;
detecting radiometric isologues of the calibration points in the three-dimensional image; and
determining rigid transformations for moving from positions of the calibration points to positions of their counterparts in the three-dimensional image.

7. The method of claim 6, wherein the calibration points comprise points of a surface of the head of the patient after installing the latter on the operating table.

8. The method of claim 1, wherein the processing of the bidimensional images to reconstitute at least partially the current cerebral arterial tree structure of the patient comprises segmenting the bidimensional images to obtain a median position of one or more of vessels and arteries of the brain so as to reconstitute at least partially the current cerebral arterial tree structure of the patient.

9. The method of claim 1, wherein the determining the shift field comprises determining non-linear transformations, called elastic transformations, allowing positions of points of the reference cerebral arterial tree structure to move to corresponding positions of points of the current arterial tree structure.

10. A system for determining brain shift of a patient, comprising a computer to execute the method of claim 1.

11. The method of claim 1, further comprising verifying the estimated brain shift by:
  acquiring one or more bidimensional images of the brain of the patient; and
  calculating a position error between the points of the bidimensional images and their isologues in the compensated image generated from the estimated global shift of the brain of the patient.

12. An image-processing method for estimating a brain shift of a patient, the method comprising:
  processing a three-dimensional image of a brain of the patient, acquired prior to a surgical operation, to obtain a reference cerebral arterial tree structure of the patient;
  processing bidimensional images of the brain of the patient, acquired during the operation, to reconstitute at least partially a current cerebral arterial tree structure of the patient;
  determining, from mapping of the reference and current cerebral arterial tree structures, a shift field of a vascular tree representing a shift of a current vascular tree relative to a reference vascular tree;
  applying the determined shift field of the vascular tree to a biomechanical model of the brain of the patient for estimating the brain shift of the patient;
  generating, from the estimated brain shift, at least one image of the brain of the patient in which the brain shift is compensated; and
  verifying the estimated brain shift by acquiring one or more bidimensional images of the brain of the patient and calculating a position error between the points of the bidimensional images and their isologues in the compensated image generated from the estimated global shift of the brain of the patient.

13. The method of claim 12, further comprising calculating disparities between generated points of the compensated image of the brain and one or more bidimensional control images acquired during the surgical operation.

14. The method of claim 12, wherein:
  the three-dimensional image acquired prior to the surgical operation includes a magnetic resonance angiography image, and
  the bidimensional images acquired during the surgical operation include ultrasound images in Doppler mode.

15. The method of claim 12, wherein the processing of the three-dimensional image to obtain the reference cerebral arterial tree structure comprises orienting the three-dimensional image relative to a head of the patient after installing the latter on an operating table.

16. The method of claim 15, wherein the orienting of the three-dimensional image comprises:
  locating a set of calibration points on the head of the patient after installing the latter on the operating table;
  detecting radiometric isologues of the calibration points in the three-dimensional image; and
  determining rigid transformations for moving from positions of the calibration points to positions of their counterparts in the three-dimensional image.

17. The method of claim 16, wherein the calibration points comprise points of a surface of the head of the patient after installing the latter on the operating table.

18. The method of claim 12, wherein the processing of the bidimensional images to reconstitute at least partially the current cerebral arterial tree structure of the patient comprises segmenting the bidimensional images to obtain a median position of one or more of vessels and arteries of the brain so as to reconstitute at least partially the current cerebral arterial tree structure of the patient.

19. The method of claim 12, wherein the determining the shift field comprises determining non-linear transformations, called elastic transformations, allowing positions of points of the reference cerebral arterial tree structure to move to corresponding positions of points of the current arterial tree structure.

20. An image-processing method for estimating a brain shift of a patient, the method comprising:
  processing a three-dimensional image of a brain of the patient, acquired prior to a surgical operation, to obtain a reference cerebral arterial tree structure of the patient;
  processing bidimensional images of the brain of the patient, acquired using a probe during the operation, to reconstitute at least partially a current cerebral arterial tree structure of the patient;
  determining, from mapping of the reference and current cerebral arterial tree structures, a shift field of a vascular tree representing a shift of a current vascular tree relative to a reference vascular tree;
  applying the determined shift field of the vascular tree to a biomechanical model of the brain of the patient for estimating the brain shift of the patient; and
  generating, from the estimated brain shift, at least one image of the brain of the patient in which the brain shift is compensated.

* * * * *